US00PP10150P

United States Patent [19]

Moore

[11] Patent Number: Plant 10,150

[45] Date of Patent: Dec. 16, 1997

[54] POLYANTHA ROSE PLANT NAMED 'MORREDFAR'

[76] Inventor: Ralph S. Moore, 2519 E. Noble Ave., Visalia, Calif. 93292

[21] Appl. No.: 717,751

[22] Filed: Sep. 23, 1996

[51] Int. Cl.[6] ..... A01H 5/00

[52] U.S. Cl. ..... Plt./28

[58] Field of Search ..... Plt./1, 28, 22, Plt./27, 10

*Primary Examiner*—Howard J. Locker

[57] ABSTRACT

This invention relates to a new and distinct cultivar of polyantha rose, primarily identified by the red color of its petals, spreading growth habit and double flowers.

2 Drawing Sheets

The present invention relates to a new and distinct cultivar of hardy, bush type rose plant of the polyantha class. The cultivar is primarily characterized as to novelty by its red color, spreading plant habit and double flowers. The cultivar is further characterized by:

An abundance of blooms, with flowers usually borne in clusters and sprays;

Little or no fragrance;

A plant of vigorous, spreading growth habit, with semi-glossy foliage with pointed leaflets; the buds and flowers being similar in form and size to 'The Fairy' (polyantha) but differing in color, being red instead of pink; and A plant which grows and blooms satisfactorily both in greenhouse and outdoors; with good repeat bloom, is good for growing in large pots and provides excellent garden decoration as a ground cover or flowering shrub.

The present cultivar of polyantha rose was originated by me at my nursery, located at Visalia, Calif., under conditions of careful control and observation, as a result of a cross of Simon Robinson as the seed parent × Simon Robinson as the pollen parent. NOTE: Simon Robinson (miniature) is a low growing plant with single (5 petal) 1½ inch pink flowers. Said to be from a cross of *Rosa wichuraiana* × New Penny.

Subsequent to my origination of the cultivar I successfully asexually reproduced this new cultivar at my nursery, located as aforementioned, by budding as well as by cuttings; the reproductions have run true in all respects.

BRIEF DESCRIPTION OF THE PHOTOGRAPHIC ILLUSTRATIONS

The new and distinct rose cultivar may be further described by reference to the accompanying two sheets of photographic illustrations.

Sheet 1 is a whole plant view of the cultivar grown as a weeping tree, showing flowers and foliage.

Sheet 2 shows in more detail an individual cluster of flowers.

Plant part coloration illustrated is as true as is reasonably possible to attain in photographic illustrations of this type.

Referring now specifically to the new and distinct cultivar of polyantha rose plant, the following is a detailed description thereof in outline; all major color plate identification being by reference to The *R.H.S. Colour Chart* (Royal Horticultural Society) except where common terms of color definition are employed.

Type: Hardy; spreading; seedling; outdoors; ground cover; cut flowers; garden decoration; potted plant.

Class: Polyantha.

*Cultivar identification.*—'MORredfar'.

*Commercial synonym.*—'Red Fairy'.

Flowers borne: In clusters and sprays on sturdy wiry stems.

Quantity of bloom: Abundant both outside and inside greenhouse.

Bud:

*Peduncle.*—Medium length (1 inch); erect; medium green, near Green Group 143B, sometimes tinted bronze (outdoors); nearly smooth—some very short hairs.

*Before calyx breaks.*—Size-small.

*Form.*—Short, rounded, with several small foliaceous appendages on surface of the bud; with foliaceous parts extending beyond the tip of the bud equal to less than one-half its length.

*Color.*—Medium green, near Green Group 143B, occasionally tinted with bronze (outdoors). As calyx breaks—Color—near Red 47A. Opening—Opens well in all weather.

Bloom:

*Size when fully open.*—Small, averaging about 25–30mm (or 1-1¼").

*Petalage.*—Double—averaging about 20 to 30 petals, arranged regularly plus several small petaloids.

*Form.*—Full, informal at first, becoming rounded with petals rolled loosely outward and downward. Fully opened flowers may show stamens.

*Sepals.*—Permanent; spear shaped; recurved.

*Behavior.*—Long lasting on plant; spent petals or flowers drop off.

*Flower longevity* (July and August 1996)—Plant in pot—5–7 days or longer. Cut flowers at living room temperature—4–5 days.

*Petals.*—Fairly thick; satiny on inside and on outside surface.

*Shape.*—Outside petals—broad lanceolate with rounded tip. Intermediate—broad lanceolate with nearly round tip. Inside—Lanceolate sometimes twisted.

*Color.*—(Newly opening flower from plant grown outdoors in August, 1995, Visalia, Calif. (photograph taken Spring 1995)). Outside petal—Outside surface—near Red 54B. Inside surface—near Red 53B often with white streak (line) down center of petal. Intermediate petal—Outside surface similar to outside petal; Inside surface similar to outside petal. Inner petal—Outside surface similar to intermediate petal. Inside surface similar to intermediate petal.

*General color effect.*— Newly opened flowers—Medium red. Three days open—color is similar to fresh open flower, but may be lighter and less bright. Flower (petal) color becomes progressively lighter as the flowers age.

Reproductive organs:

*Stamens.*—Moderately abundant, arranged regularly about the pistil.

*Filaments.*—Very short, varying length.

*Anthers.*—Well formed, yellow.

*Pollen.*—Some.

*Pistils.*—Average number, bunched, even, greenish.

*Styles.*—Short; pale greenish.

*Ovaries.*—All enclosed in calyx.

*Hips.*—Some, small.

Foliage:

*Leaves.*—Compound of five (sometimes 3 or 7) leaflets; medium small; leathery; semi-glossy.

*Leaflets.*—Shape: Broad lanceolate; (ovoid) apex acute; base-rounded. Color: Medium green. Rachis: Medium strength; upper side smooth; grooved; underside may have several small thorns (or claws). Stipules: Medium to long length; medium width; short length narrow points which turn out usually at about 45° or more. Color similar to leaflets.

*Habit.*—Bushy; spreading; much branched with tendency to droop as foliage and flowers mature, thus giving the plant a spreading profile suitable for ground cover, tub or hanging basket use.

*Growth.*—Vigorous; internodes moderately short.

*Canes.*—Medium slender; sturdy.

*Main stems.*—Color: Medium green, near Green Group 143B.

*Thorns.*—Average of varying size and length, usually hooked downward, color: brown. Hairs—few or none.

Note:

(1 ) As compared with 'The Fairy' the flowers of the present cultivar are red rather than pink and the plant more vigorous and more spreading.

(2) As compared with 'Flower Carpet' (U.S. Plant Pat. No. 7,282) the present cultivar is more vigorous, with larger foliage and of a lighter green color. Also, 'Flower Carpet' has pink flowers of larger size (2½") size, whereas my present rose has smaller (1¼") flowers and in more abundance.

The polyantha rose plant and its flowers as heretofore described may vary in slight detail due to climate, soil and cultural conditions under which the cultivar may be grown; the present description being of the cultivar as grown at Visalia, Calif.

The following is claimed:

1. A new and distinct cultivar of rose plant of the polyantha class, of hardy, much branched, spreading habit substantially as illustrated and described, characterized by buds and flowers, basically red, the bud being rounded in the early stage, resembling in form 'The Fairy' (polyantha), with the open flowers being double and rounded with about 20 to 30 petals plus several small petaloids; and further characterized by a plant of compact, vigorous, spreading habit with main stems and shoots of average thorniness, the said plant being easy to propagate from soft wood cuttings and by budding with an abundance of medium to small semi-glossy foliage, the flowers being usually borne in clusters or sprays of 25 to 50 or more per stem.

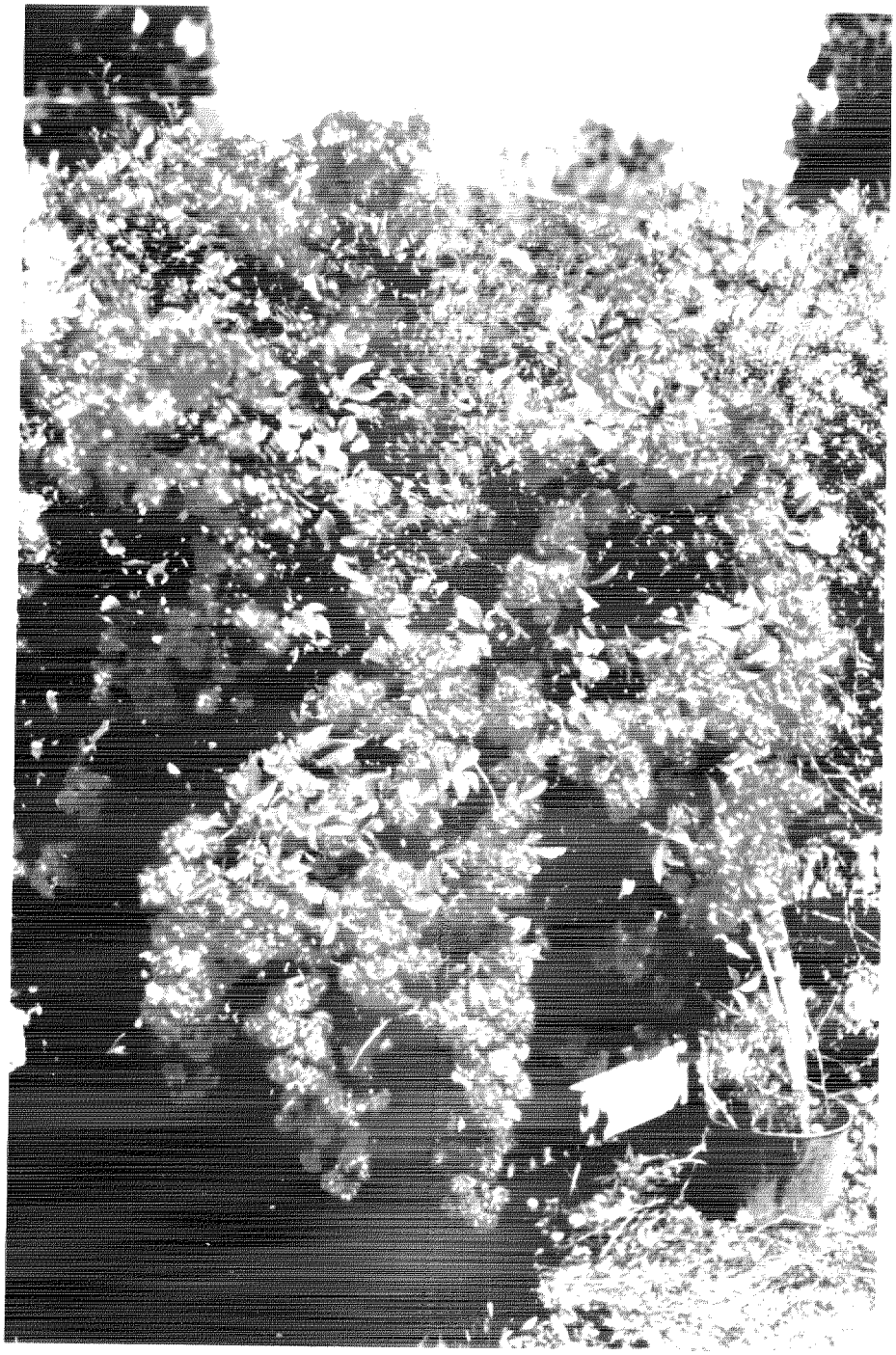

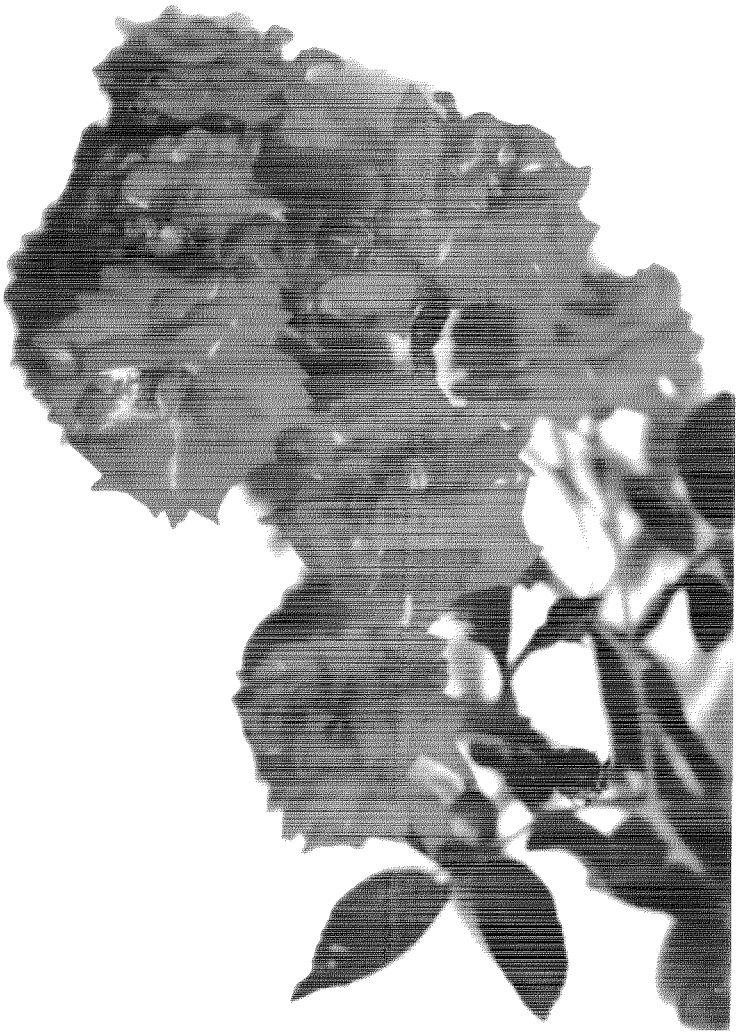

* * * * *